US012708263B2

(12) United States Patent
Tanabe et al.

(10) Patent No.: US 12,708,263 B2
(45) Date of Patent: Aug. 18, 2026

(54) OPHTHALMIC DEVICE, OPHTHALMIC DEVICE CONTROL METHOD, AND PROGRAM

(71) Applicant: NIKON CORPORATION, Tokyo (JP)

(72) Inventors: Yasushi Tanabe, Fujisawa (JP); Yasufumi Nishi, Edinburgh (GB)

(73) Assignee: NIKON CORPORATION, Tokyo (JP)

( * ) Notice: Subject to any disclaimer, the term of this patent is extended or adjusted under 35 U.S.C. 154(b) by 242 days.

(21) Appl. No.: 18/554,140

(22) PCT Filed: Apr. 8, 2022

(86) PCT No.: PCT/JP2022/017409
§ 371 (c)(1),
(2) Date: Oct. 5, 2023

(87) PCT Pub. No.: WO2022/215755
PCT Pub. Date: Oct. 13, 2022

(65) Prior Publication Data

US 2025/0072746 A1 Mar. 6, 2025

(30) Foreign Application Priority Data

Apr. 8, 2021 (JP) ................................ 2021-066040

(51) Int. Cl.
*A61B 3/10* (2006.01)
*G16H 50/20* (2018.01)

(52) U.S. Cl.
CPC ............ *A61B 3/102* (2013.01); *G16H 50/20* (2018.01)

(58) Field of Classification Search
CPC ................................ A61B 3/102; G16H 50/20
(Continued)

(56) References Cited

U.S. PATENT DOCUMENTS

2007/0291277 A1* 12/2007 Everett .............. G01B 9/02077 356/497
2012/0249961 A1* 10/2012 Muto ..................... A61B 3/152 351/208
(Continued)

FOREIGN PATENT DOCUMENTS

JP 2013-076587 A 4/2013
JP 2015-070919 A 4/2015
(Continued)

OTHER PUBLICATIONS

Extended European Search Report issued in corresponding EP Application No. 22784737.3 Dated Mar. 3, 2025 (5 pages).
(Continued)

*Primary Examiner* — Mohammed A Hasan
(74) *Attorney, Agent, or Firm* — Foley & Lardner LLP

(57) ABSTRACT

An ophthalmic device including an interference optical system that detects interference light between signal light obtained by scanning an examined eye with light from a light source and reference light configured from light divided from the light source, an adjustment section that is disposed on an optical path of at least one out of the signal light or the reference light, and that adjusts a polarization state of light propagating along the at least one optical path such that a polarization state of the signal light is the same as the polarization state of the reference light, and a control section that controls the adjustment section according to a scan angle scanned on the examined eye.

10 Claims, 12 Drawing Sheets

(58) Field of Classification Search
USPC .......................................................... 351/215
See application file for complete search history.

(56) References Cited

U.S. PATENT DOCUMENTS

| | | | | |
|---|---|---|---|---|
| 2015/0216408 | A1 | 8/2015 | Brown et al. | |
| 2015/0272432 | A1* | 10/2015 | Satake | A61B 3/0025 351/246 |
| 2015/0272435 | A1* | 10/2015 | Ito | A61B 3/14 351/206 |
| 2016/0278635 | A1* | 9/2016 | Fukuma | A61B 3/0025 |
| 2016/0278636 | A1* | 9/2016 | Fukuma | A61B 3/132 |
| 2020/0054212 | A1 | 2/2020 | Ohmura | |
| 2021/0027467 | A1* | 1/2021 | Hirokawa | G06T 7/0012 |

FOREIGN PATENT DOCUMENTS

| | | | |
|---|---|---|---|
| JP | 2015-534482 | A | 12/2015 |
| JP | 2017-184874 | A | 10/2017 |
| JP | 2018-102789 | A | 7/2018 |
| JP | 2019-080804 | A | 5/2019 |
| JP | 2021-112610 | A | 8/2021 |
| JP | 2022-161320 | A | 10/2022 |

OTHER PUBLICATIONS

Japanese Office Action and translation issued in JP Application No. 2025-061210 dated Dec. 2, 2025 (6 pages).

European Extended Search Report issued in corresponding European Patent Application No. 25226290.2 dated Mar. 16, 2026.

* cited by examiner

FIG.1

100
110
OPHTHALMIC DEVICE
120
EYE AXIAL LENGTH MEASUREMENT DEVICE
130
140
150
156

110
130
16
CONTROL DEVICE
CPU
RAM
ROM
16A
16B
16C
17A
INPUT/DISPLAY DEVICE
16E
16D
I/O
17
STORAGE DEVICE
DATA PROCESSING PROGRAM
COMMUNI - CATION I/F
15
14
18
SLO UNIT
LIGHT SOURCE
18A
DETECTION ELEMENT
18B
18C
WIDE ANGLED OPTICAL SYSTEM
19
FIRST OPTICAL SCANNER
22
SECOND OPTICAL SCANNER
24
26
COMMON OPTICAL SYSTEM
28
THIRD OPTICAL SCANNER
29
OCT UNIT
20
LIGHT SOURCE
20A
SENSOR
20B
20C
20D
20E
20F
20G
27
12
12A
O
θ
Y
Z
X

OCT UNIT
20
SECOND OPTICAL SCANNER
24
P1
26
SCANNING DEVICE
19
FIRST OPTICAL SCANNER
22
P1
SLO UNIT
18
THIRD OPTICAL SCANNER
29
P2
(P3)
28
30
30A
32
32A
12
12A
P4
O
Y
Z
X

START
INSTALL MODEL EYE
S100
SET SCAN RANGE
S102
SET SCAN ANGLE TO INITIAL VALUE
S104
SCAN MODEL EYE
S106
STORE POLARIZATION STATE
S108
DERIVE ADJUSTMENT AMOUNT OF POLARIZATION ADJUSTMENT SECTION
S110
ASSOCIATE AND STORE SCAN ANGLE, POLARIZATION STATE, AND ADJUSTMENT AMOUNT
S112
SCANNING COMPLETE?
S114
N
Y
S116
UPDATE SCAN ANGLE
GENERATE TABLE
S118
END

FIG.6

TBw

| SCAN ANGLE (EXTERNAL ILLUMINATION ANGLE $\theta$) | −70 | −60 | −50 | −40 | −30 | −20 | −10 | ±0 | 10 | 20 | 30 | 40 | 50 | 60 | 70 |
|---|---|---|---|---|---|---|---|---|---|---|---|---|---|---|---|
| POLARIZATION STATE (PZ) | $PZ_{-70}$ | $PZ_{-60}$ | $PZ_{-50}$ | $PZ_{-40}$ | $PZ_{-30}$ | $PZ_{-20}$ | $PZ_{-10}$ | $PZ_{0}$ | $PZ_{10}$ | $PZ_{20}$ | $PZ_{30}$ | $PZ_{40}$ | $PZ_{50}$ | $PZ_{60}$ | $PZ_{70}$ |
| ADJUSTMENT AMOUNT (W) | $W_{-70}$ | $W_{-60}$ | $W_{-50}$ | $W_{-40}$ | $W_{-30}$ | $W_{-20}$ | $W_{-10}$ | $W_{0}$ | $W_{10}$ | $W_{20}$ | $W_{30}$ | $W_{40}$ | $W_{50}$ | $W_{60}$ | $W_{70}$ |

TBv

| SCAN ANGLE (EXTERNAL ILLUMINATION ANGLE $\theta$) | −70 | −60 | −50 | −40 | −30 | −20 | −10 | ±0 | 10 | 20 | 30 | 40 | 50 | 60 | 70 |
|---|---|---|---|---|---|---|---|---|---|---|---|---|---|---|---|
| ADJUSTMENT AMOUNT (W) AT MAXIMUM CONTRAST | $V_{-70}$ | $V_{-60}$ | $V_{-50}$ | $V_{-40}$ | $V_{-30}$ | $V_{-20}$ | $V_{-10}$ | $V_0$ | $V_{10}$ | $V_{20}$ | $V_{30}$ | $V_{40}$ | $V_{50}$ | $V_{60}$ | $V_{70}$ |

OPHTHALMIC DEVICE, OPHTHALMIC DEVICE CONTROL METHOD, AND PROGRAM

CROSS-REFERENCE TO RELATED APPLICATIONS

This application is a National Stage of International Application No. PCT/JP2022/017409, filed Apr. 8, 2022, the disclosure of which is incorporated herein by reference in its entirety. Further, this application claims priority from Japanese Patent Application No. 2021-066040, filed Apr. 8, 2021, the disclosure of which is incorporated herein by reference in its entirety.

TECHNICAL FIELD

The technology disclosed herein relates to an ophthalmic device, a control method for an ophthalmic device, and a program.

BACKGROUND ART

A hitherto known optical image measuring device acquires a fundus tomographic image based interference light between signal light that has passed through an examined eye and signal light. There has hitherto been a demand to adjust the polarization states of signal light and reference light (see, for example, Japanese Patent Application Laid-Open (JP-A) No. 2015-70919).

SUMMARY OF INVENTION

An ophthalmic device of a first aspect of technology disclosed herein includes an interference optical system that detects interference light between signal light obtained by scanning an examined eye with light from a light source and reference light configured from light divided from the light source, an adjustment section that is disposed on an optical path of at least one of the signal light or the reference light, and that adjusts a polarization state of light propagating along the at least one optical path such that a polarization state of the signal light is the same as a polarization state of the reference light, and a control section that controls the adjustment section according to a scan angle at which the examined eye is scanned.

A control method for controlling the ophthalmic device of a second aspect of technology disclosed herein is a control method performed by a processor of the ophthalmic device. The control method includes a step of acquiring an adjustment amount of the adjustment section that is disposed on the optical path of the at least one of the signal light or the reference light, and that adjusts the polarization state of the light propagating along the at least one optical path such that the polarization state of the signal light is the same as the polarization state of the reference light, wherein the adjustment amount corresponds to a scan angle of OCT signal light, and a step of controlling the adjustment section based on the adjustment amount.

A program of a third aspect of technology disclosed herein causes a computer to execute acquiring an adjustment amount of an adjustment section that is disposed on an optical path of at least one of a signal light or a reference light, and that adjusts a polarization state of light propagating along the at least one optical path such that a polarization state of the signal light is the same as a polarization state of the reference light, wherein the adjustment amount corresponds to a scan angle of OCT signal light; and controlling the adjustment section based on the adjustment amount.

BRIEF DESCRIPTION OF DRAWINGS

FIG. 1 is a block diagram illustrating an example of a configuration of an ophthalmic system.

FIG. 6 is a sketch illustrating an example of content of a table.

FIG. 9 is a flowchart illustrating an example of a flow of table generation processing.

FIG. 11 is an sketch illustrating an example of content of a table.

DESCRIPTION OF EMBODIMENTS

Figure 2:
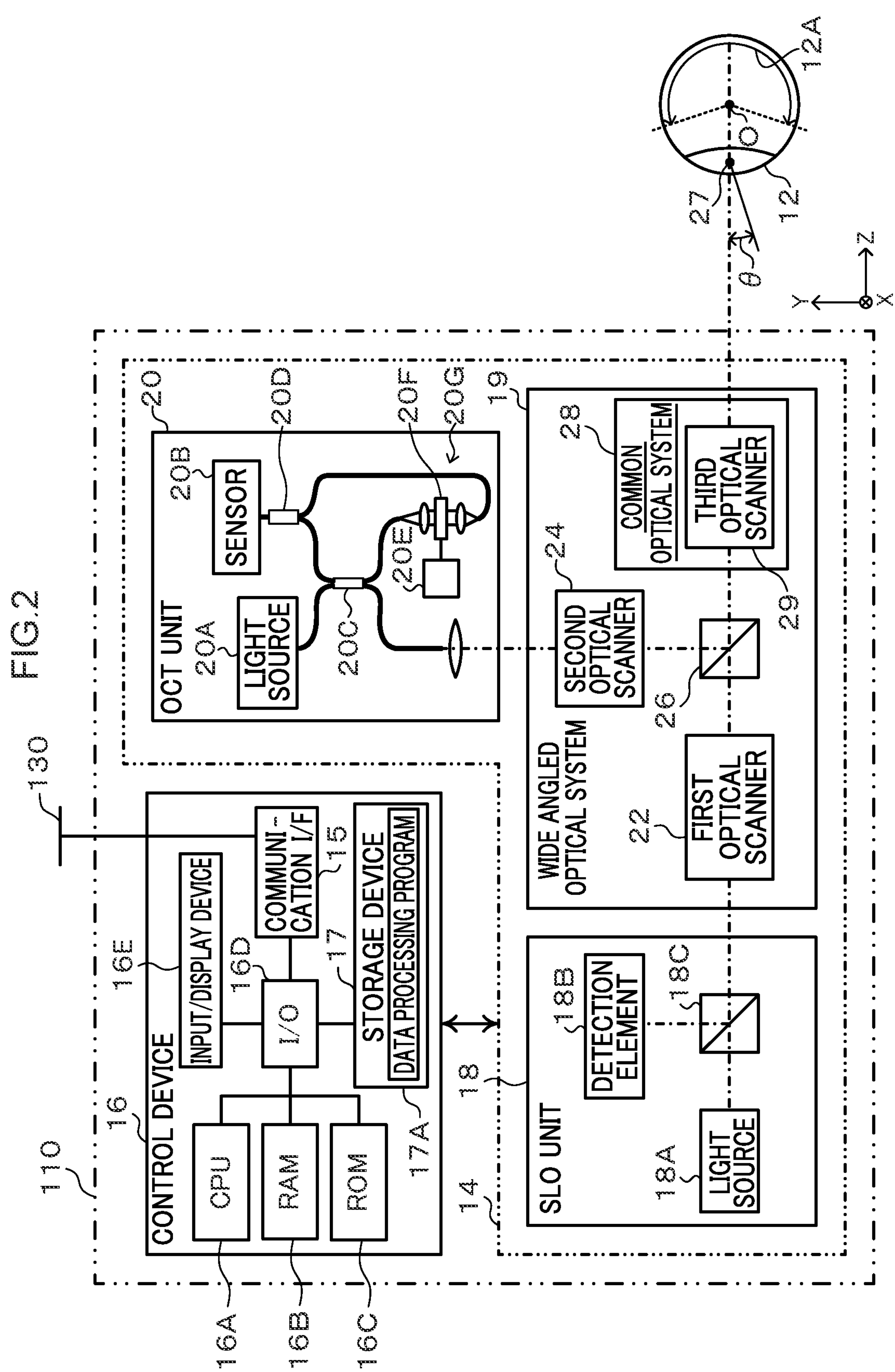
FIG. 2 is a schematic configuration diagram illustrating an example of an overall configuration of an ophthalmic device.

Detailed description follows regarding exemplary embodiments of the present invention, with reference to the drawings. In the following, for ease of explanation a scanning laser ophthalmoscope will be referred to as "SLO". Moreover, for ease of explanation optical coherence tomography will be referred to as "OCT".

First Exemplary Embodiment

An example of a configuration of an ophthalmic system 100 will now be described with reference to FIG. 1.

Figure 1:
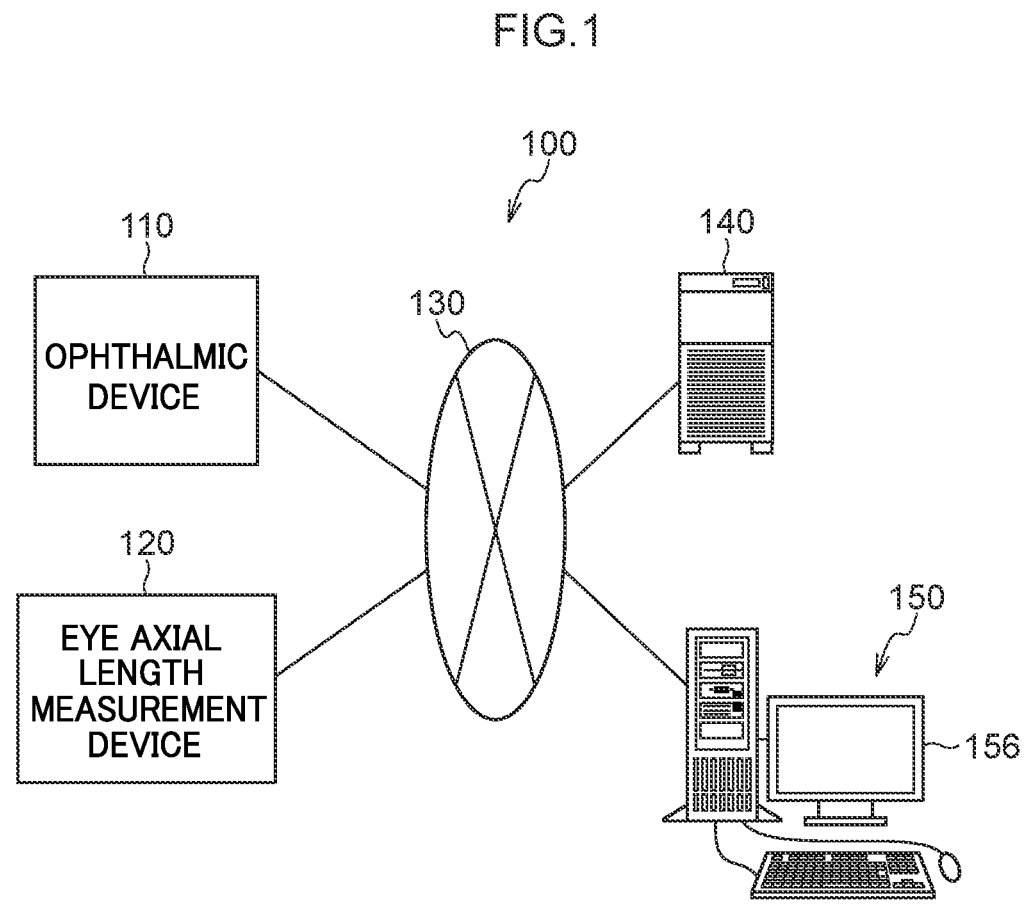

As illustrated in the example of FIG. 1, the ophthalmic system 100 includes an ophthalmic device 110, an eye axial length measurement device 120, a server device (hereafter referred to as "server") 140, and an image display device (hereafter referred to as "viewer") 150. The ophthalmic device 110 acquires fundus images and tomographic images. The eye axial length measurement device 120 measures the eye axial length of an examinee. The server 140 stores plural fundus images, obtained by imaging the fundus of plural examinees using the ophthalmic device 110, and eye axial lengths, in association with IDs of the examinees. The viewer 150 displays fundus images acquired by the server 140 and data obtained by analyzing fundus images. The fundus images include SLO fundus images imaged by SLO, OCT images (also called tomographic images) imaged by OCT, and the like.

The ophthalmic device 110, the eye axial length measurement device 120, the server 140, and the viewer 150 are all interconnected over a network 130.

Next, description follows regarding a configuration of the ophthalmic device 110, with reference to FIG. 2.

As illustrated in FIG. 2, the ophthalmic device 110 includes an imaging device 14 and a control device 16. The imaging device 14 images the fundus of an examined eye. The control device 16 is realized by a computer including a central processing unit (CPU) 16A, random access memory (RAM) 16B, read only memory (ROM) 16C, and an input/output (I/O) port 16D.

The ophthalmic device 110 is an example of an ophthalmic device of technology disclosed herein.

A storage device 17 is connected to the input/output (I/O) port 16D. Note that the storage device 17 is configured, for example, by non-volatile memory (NVM). The input/output (I/O) port 16D is connected to the network 130 through a communication interface (I/F) 15.

The control device 16 includes an input/display device 16E connected to the CPU 16A through the I/O port 16D. The input/display device 16E displays images obtained by imaging, and includes a graphical user interface to receive various instructions include an imaging instruction. Examples of the graphical user interface include a touch panel display.

A data processing program 17A is stored in the storage device 17. Note that although explanation follows of a case in which the data processing program 17A is stored in the storage device 17, the technology disclosed herein is not limited thereto, and the data processing program 17A may be stored in the ROM 16C.

The data processing program 17A is an example of an ophthalmic program of technology disclosed herein.

In the following description, when the ophthalmic device 110 is installed on a horizontal plane, the horizontal direction is referred to as the "X direction", a direction perpendicular to the horizontal direction is referred to as the "Y direction", and a direction connecting a pupil center 27 at the anterior segment of an examined eye 12 and an eyeball center O of an eyeball is referred to as the "Z direction". Accordingly, the X direction, Y direction, and Z direction are mutually perpendicular directions.

Description follows regarding the imaging device 14. The imaging device 14 operates under control of the control device 16. The imaging device 14 includes an SLO unit 18, a wide angled optical system 19, and an OCT unit 20.

The wide angled optical system 19 includes a common optical system 28 that includes a first optical scanner 22 configured by a polygon mirror or the like that deflects light from the SLO unit 18 in the X direction (horizontal direction), a second optical scanner 24 configured by a mirror galvanometer or the like that deflects light from the OCT unit 20 in the X direction (horizontal direction), a dichroic mirror 26, and a third optical scanner 29 configured by a mirror galvanometer or the like that deflects light in the Y direction (vertical direction). An optical path of SLO light and an optical path of OCT light are combined by the dichroic mirror 26, and the SLO light and the OCT light are shone through a pupil of the examined eye 12 via the common optical system 28 and onto an imageable region 12A of the fundus. Note that the imageable region 12A is within a range of about 200 degrees when converted into an internal illumination angle from the eyeball center O.

The SLO unit 18 is configured including a light source 18A, a detection element 18B, a dichroic mirror 18C and the like, and is configured so as to image the fundus of the examined eye 12. The light source 18A includes a light source for red light (R light), a light source for green light (G light), a light source for blue light (B light), and a light source for infrared rays (for example, near-infrared light), and is configured so as to be able so switch between modes emitting R light, G light, and/or B light, and a mode emitting infrared rays (for example, near-infrared rays).

Light from the light source 18A (hereafter referred to as "SLO light") passes through the dichroic mirror 18C toward the wide angled optical system 19. The SLO light is deflected by the first optical scanner 22 in the X direction (horizontal direction), passes through the dichroic mirror 26, and is deflected by the third optical scanner 29 of the common optical system 28 in the Y direction (vertical direction). The first optical scanner 22 and the third optical scanner 29 are controlled by the control device 16 so as to scan the imageable region 12A of the fundus. Reflected light from the fundus passes through the wide angled optical system 19, is reflected by the dichroic mirror 18C, and is photo-detected by the detection element 18B. SLO fundus images (hereafter referred to as "SLO images") that are en face images of the fundus are generated by the control device 16 from detection signals from the detection element 18B.

The OCT unit 20 will be described for an example of a Fourier domain OCT. In particular, the ophthalmic device 110 according to technology disclosed herein includes the OCT unit 20 for swept-source OCT (SS-OCT) using a wavelength swept-source.

The OCT unit 20 includes a reference light optical system 20G including a light source 20A, a sensor 20B, fiber couplers 20C, 20D, and a polarization adjustment section 20F. The light source 20A is a wavelength swept-source light source that emits light in a near-infrared wavelength region.

Light from the light source 20A of the OCT unit 20 (hereafter referred to as signal light (LS)) branches at the fiber coupler 20C, with one branch of the signal light being deflected in the X direction (horizontal direction) by the second optical scanner 24 of the wide angled optical system 19, reflected by the dichroic mirror 26, and deflected in the Y direction (vertical direction) by the third optical scanner 29 of the common optical system 28. The second optical scanner 24 and the third optical scanner 29 are controlled by the control device 16, and a region where OCT imaging is to be performed on the imageable region 12A of the fundus is scanned. The region to perform OCT imaging is specified by a user of the ophthalmic device 110 or the like. There are various scan patterns for such scanning, such as an A-scan that is a scan of a single point on the fundus, a line shaped B-scan for acquiring a tomographic image of the fundus, and a plane shaped C-scan for acquiring OCT volume data.

The signal light reflected from the fundus is introduced to the fiber coupler 20D through the wide angled optical system 19 and the fiber coupler 20C. Moreover, the other part of the signal light, namely signal light that proceeds through the light source 20A, the fiber coupler 20C, the polarization adjustment section 20F, and the sensor 20B, is called reference light (LR). The other reference light branched at the fiber coupler 20C is adjusted in polarization state by the polarization adjustment section 20F and is incident to the fiber coupler 20D. The reference light configured with adjusted polarization is caused to interfere with the signal light reflected from the fundus using the fiber coupler 20D, and the interference light is incident to the sensor 20B. The sensor 20B detects an intensity of the interference light at each wavelength, and outputs these intensities as a detection signal to the control device 16.

The control device 16 performs processing such as Fourier transformation or the like on the detection signal of the sensor 20B, and generates a tomographic image that is an OCT image, hereafter referred to as an "OCT image".

An optical path length of the signal light (LS) is determined by a path length from the light source 20A to the fundus and from the fundus to the sensor 20B. The optical path length of the reference light is then also controlled so as to be the same as the optical path length of the signal light.

Note that from out of the signal light, reflected light incident to the fiber coupler 20D of signal light reflected from the fundus is, in particular, called return light.

The OCT unit 20 is an example of an interference optical system of technology disclosed herein. The polarization adjustment section 20F is an example of an adjustment section of technology disclosed herein.

In the present exemplary embodiment, the polarization adjustment section 20F is coupled to a drive section 20E, and introduced light is adjusted in polarization state according to a drive amount of the drive section 20E and emitted. The polarization state is indicated by including an azimuth angle. Note that a phase difference compared to an amplitude in orthogonal coordinates may be used to indicate the polarization state. In the present exemplary embodiment a ½ wavelength plate that imparts a phase difference (λ/2) is employed as an example of the polarization adjustment section 20F, and incident linearly polarized light is rotated by the ½ wavelength plate and emitted.

The ½ wavelength plate serving as an example of the polarization adjustment section 20F is an example of an optical member of technology disclosed herein.

In the following explanation, the SLO light and signal light are both light scanned two-dimensionally in the X direction and the Y direction, and so when there is no need to distinguish between the SLO light and the signal light in the following description, the SLO light and the signal light will be referred to collectively as "scan light".

Figure 3:
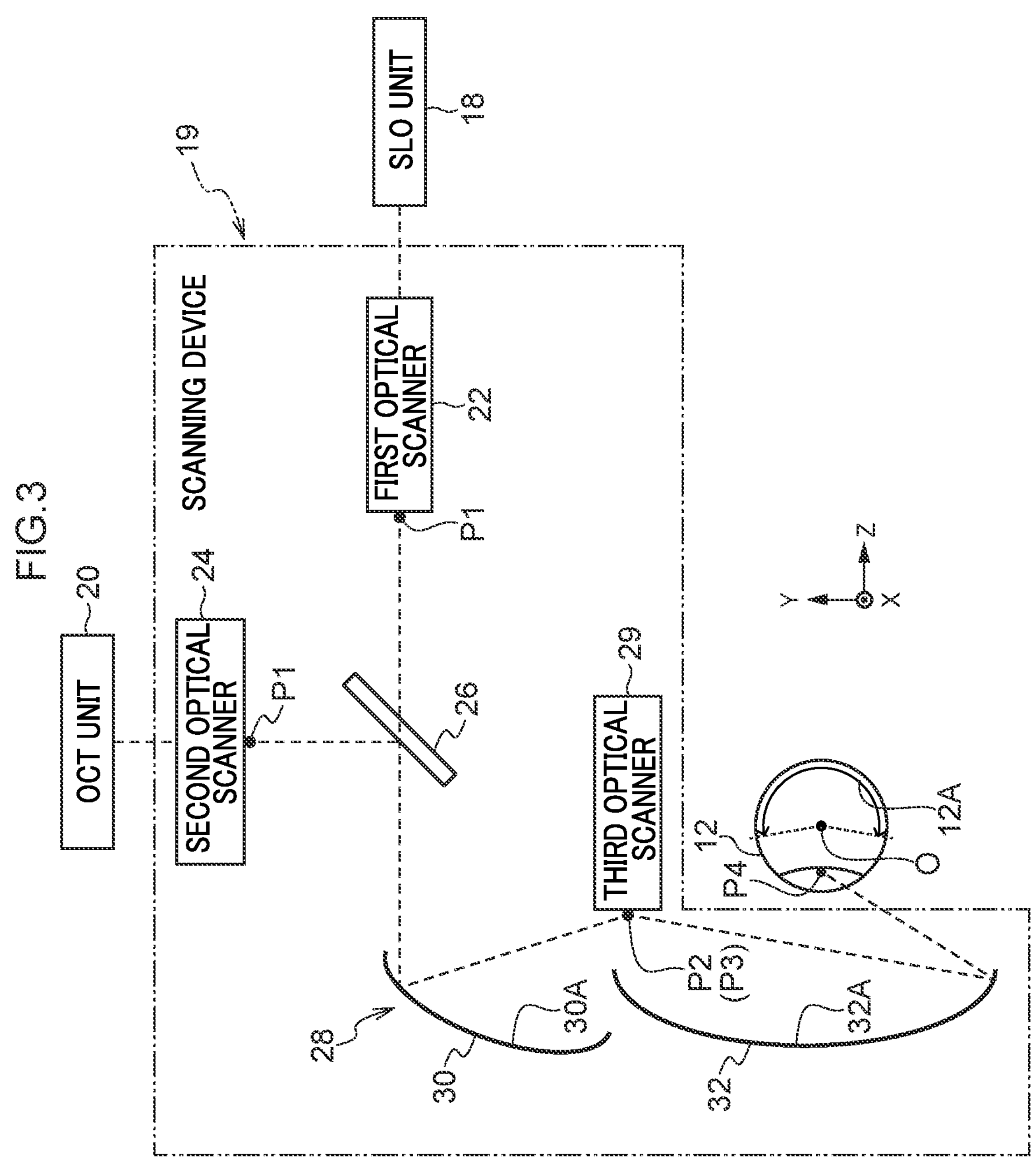
FIG. 3 is a schematic diagram illustrating an example of an schematic configuration of a wide angled optical system included in an ophthalmic device.

Next, description follows regarding a configuration of the wide angled optical system 19 included in the ophthalmic device 110, with reference to FIG. 3.

As illustrated in FIG. 3, as well as the third optical scanner 29, the common optical system 28 also includes a slit mirror 30 and an elliptical mirror 32. Note that the dichroic mirror 26, the slit mirror 30, and the elliptical mirror 32 are shown in end-on side views. Note that instead of the slit mirror 30 and the elliptical mirror 32, the common optical system 28 may be configured by using a mirror such as a convex mirror, a hyperbolic mirror, or a freely selected curvature mirror, and a group of plural lenses.

The slit mirror 30 includes a first reflection face 30A having an elliptical shape. The first reflection face 30A includes a first focal point P1 and a second focal point P2. The elliptical mirror 32 also includes a second reflection face 32A having an elliptical shape. The second reflection face 32A includes a first focal point P3 and a second focal point P4.

The slit mirror 30, the elliptical mirror 32, and the third optical scanner 29 are arranged such that the first focal point P3 and the second focal point P2 are at a common position at the third optical scanner 29. Moreover, the slit mirror 30, the elliptical mirror 32, and the third optical scanner 29 are arranged such that the second focal point P4 is positioned at a center portion of the pupil of the examined eye 12. Furthermore, the first optical scanner 22, the second optical scanner 24, and the slit mirror 30 are arranged such that the first focal point P1 is positioned at the first optical scanner 22 and at the second optical scanner 24.

Namely, the first optical scanner 22, the second optical scanner 24, and the third optical scanner 29 are arranged at conjugate positions to the center portion of the pupil of the examined eye 12.

In the present exemplary embodiment, a field of view (FOV) of the fundus is a large angle due to the wide angled optical system 19 illustrated in FIG. 3, enabling observation of a wide range fundus region. This wide range fundus region is described while distinguishing between an external illumination angle for external scan light using the ophthalmic device 110, and an internal illumination angle as an internal illumination angle inside the examined eye illuminated with the scan light. For example, an external illumination angle of 120 degrees is equivalent to an internal illumination angle of about 160 degrees. In the present exemplary embodiment the internal illumination angle is 200 degrees.

The external illumination angle is an illumination angle of light from the ophthalmic device 110 side, namely from the exterior of the examined eye 12. Namely, the external illumination angle is the angle of scan light onto the fundus of the examined eye 12 heading toward a pupil center 27 of the examined eye 12 (namely, a center point of the pupil as viewed face-on (see also FIG. 2)). The external illumination angle is equivalent to the angle of light reflected from the fundus so as to head out from the pupil center 27 and be emitted outside from the examined eye 12 toward the ophthalmic device 110.

The internal illumination angle represents an illumination angle of light effectively imageable by the scan light being illuminated onto the fundus of the examined eye 12, with respect to the eyeball center O of the examined eye 12 as a reference position. Although external illumination angles A and internal illumination angles B have correspondence relationships to each other, since the following description is a description of an ophthalmic device, the external illumination angle is employed as an illumination angle corresponding to the field of view angle of the fundus.

The ophthalmic device 110 performs imaging in the imageable region 12A (see also FIG. 2), this being a fundus region of the examined eye 12, using the external illumination angle. The imageable region 12A is, for example, the maximum region capable of being scanned by the scan light with the wide angled optical system 19.

SLO images obtained by the ophthalmic device 110 imaging the imageable region 12A of the examined eye 12 are called UWF SLO images. Note that UWF is an abbreviation for Ultra-Widefield (ultra-wide angle). A region extending from a posterior pole portion of the fundus of the examined eye 12 past an equatorial portion thereof can be imaged by the wide-angle optical system 30 having a field of view (FOV) angle of the fundus that is an ultra-wide field, enabling imaging of structural objects, such as vortex veins, present at fundus peripheral portions.

Figure 4:
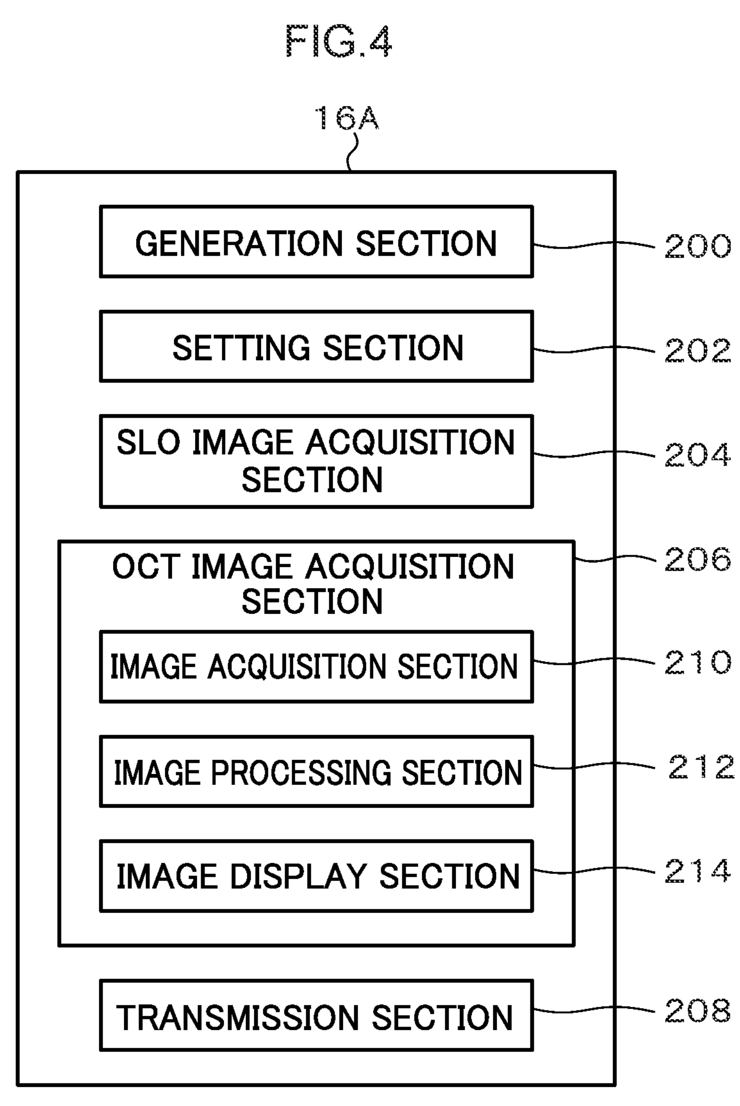
FIG. 4 is a block diagram illustrating an example of functional sections of an ophthalmic device.

Next, description follows regarding an example of various functional sections implemented by the CPU 16A of the control device 16 of the ophthalmic device 110 executing the data processing program 17A, with reference to FIG. 4.

The data processing program 17A includes a setting function, an SLO image acquisition function, an OCT image acquisition function (image acquisition function, image processing function, image display function), and a transmission function. By the CPU 16A executing the data processing program 17A including these various functions, the CPU 16A functions as a setting section 202, an SLO image acquisition section 204, an OCT image acquisition section 206 (image acquisition section 210, image processing section 212, image display section 214), and transmission section 208, as illustrated in FIG. 4.

Note that although control device 16 of the ophthalmic device 110 includes the input/display device 16E in the present exemplary embodiment, as illustrated in FIG. 2, the technology disclosed herein is not limited thereto. Configuration may be made in which, for example, the control device 16 of the ophthalmic device 110 does not include the input/display device 16E, and a separate individual display device is provided that is physically independent of the ophthalmic device 110. In such cases, the display device may include an image processing processor unit that operates under the control of the CPU 16A of the control device 16, and the image processing processor unit may be configured so as to display an SLO image or the like based on an image signal output as an instruction by the image display section 214.

(1) Generation of Table Indicating Correspondence Relationships Between Polarization and Scan Angle First, prior to employing the ophthalmic device 110 of the ophthalmic system 100, information is collected for adjusting the polarization state employed when acquiring an OCT image. The collected information is stored as a table TB, and is employed when acquiring an OCT image as described later. Note that data of the table TB (hereafter referred to as table data) may be transmitted to the server 140 and acquired from the server 140. The table data may be derived and stored at set up such as during device installation, or may be table data that is stored in the server 140 and then acquired therefrom.

Note that the table TB is an example of a table of technology disclosed herein.

As described above, prior to executing OCT imaging processing, information is collected for adjusting the polarization state used when acquiring OCT images. Details will now be described regarding the information collected. The information for adjusting the polarization state is information indicating adjustment of a relationship between the polarization state of the signal light and the polarization state of the reference light when acquiring an OCT image in a preferable state.

In OCT, optical coherence tomography is performed on interference light obtained by causing each return light obtained by shining signal light through the pupil of the examined eye 12 onto the fundus to interfere with the reference light. A tomographic region is imaged by performing optical coherence tomography in this manner, and an OCT image illustrating the tomographic region is acquired by the image acquisition section 210.

When the return light and the reference light interfere with each other, ideally the polarization state of the signal light and the polarization state of the reference light are equivalent. However, sometimes in OCT the polarization states of the measurement light and the reference light do not match (for example in direction of polarization), and an interference action is suppressed in a situation in which the polarization states do not match, leading to a drop in contrast of the resulting OCT image. For example, in cases in which signal light that is clockwise rotating circular polarized light is shone onto the fundus of the examined eye, suppose that the eyeball does not have birefringence, then the return light reflected at the fundus of the examined eye will be counterclockwise circular polarized light. Moreover, due to the amount of change in polarization varying according to the scan angle corresponding to the external illumination angle, the amount of change in polarization varies according to the imaging region on the fundus. Moreover, in a configuration employing an elliptical mirror as the wide angled optical system 19 as illustrated in FIG. 3, sometimes this is not perfect elliptical surface due to limits in accuracy when manufacturing the 30A and the 32A reflection faces of the elliptical mirror. Furthermore, in individual ophthalmic devices 110 too, there may be variation in the shape of the elliptical surface of the elliptical mirror in plural ophthalmic devices 110 due to tolerances during elliptical mirror manufacture or the like. Different polarization states accordingly result in the respective ophthalmic devices 110 due to variation in the shape during such elliptical mirror manufacture.

This means that interference between the signal light (return light) and the reference light is suppressed by variation in the polarization state of the signal light (return light) in cases in which the polarization state of the reference light is maintained as a fixed polarization state, with this leading to a deterioration in the quality of OCT images imaged using OCT. A polarization state is accordingly preferably made common for both the signal light according to scan angle when the signal light is scanned and the reference light. Moreover, a polarization state is accordingly preferably made common for both the signal light according to fundus position (hereafter referred to as scan position) when the signal light is scanned and the reference light. The effect can be suppressed by varying the overall optical path length of the signal light and return light according to scan position when the fundus, which is a spherical surface, is scanned with signal light passing through the center of the pupil distanced from a center of the eyeball.

Relationships between scan angles and polarization states of signal light at these scan angles can be derived in advance. Then, based on these relationships between scan angles and the polarization states of signal light at these scan angle, the polarization state can be made common for both the signal light and the reference light by performing adjustment so as to suppress difference between the polarization state of the signal light at each of the scan angles and the polarization state of the reference light. Relationships between scan angles and the polarization state of signal light at these scan angles are pre-generated as a table, and the polarization state is adjusted according to the scan angle when acquiring an OCT image.

Figure 5:
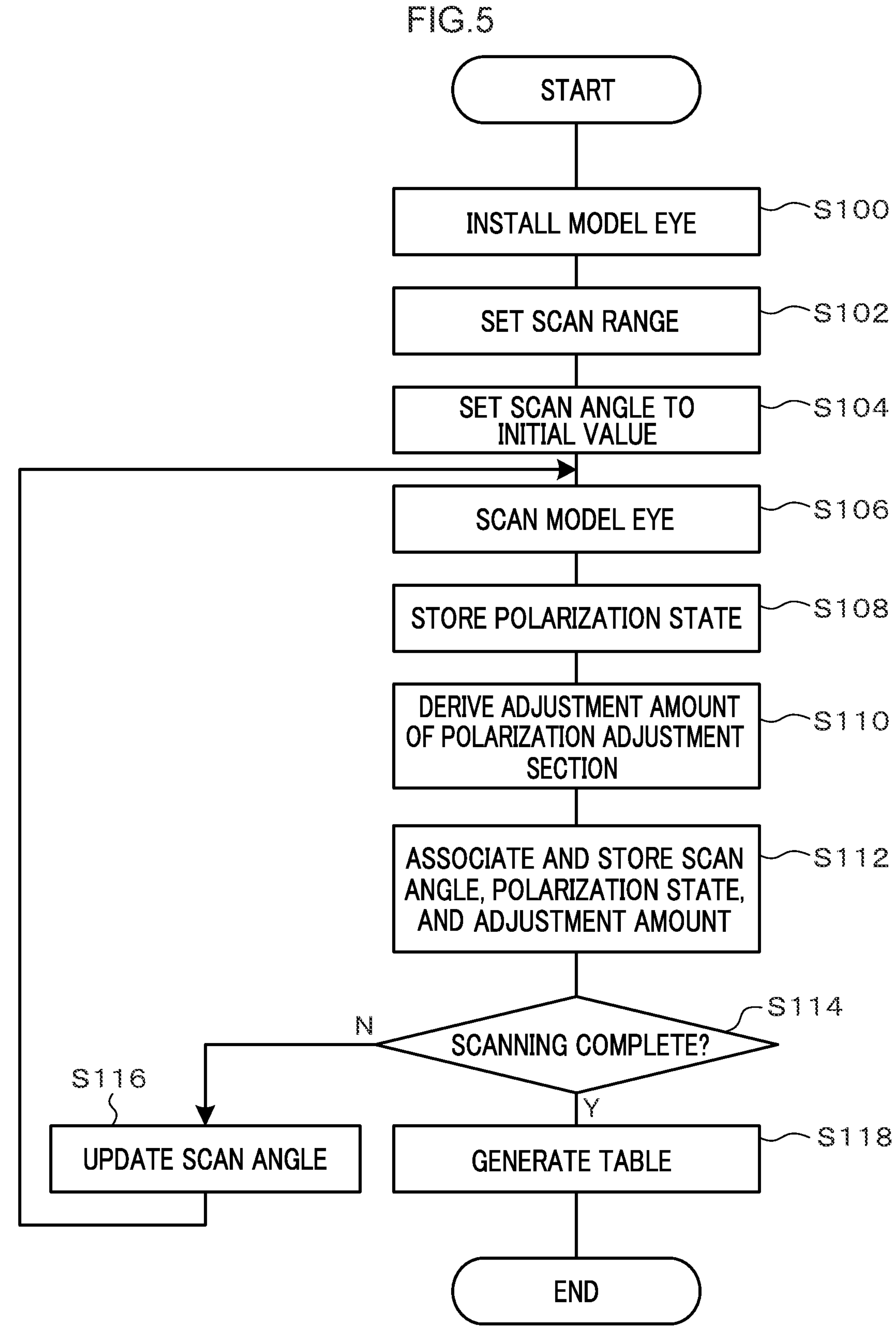
FIG. 5 is a flowchart illustrating an example of a flow of table generation processing.

Next, description follows regarding an example of processing to generate the table TB, with reference to FIG. 5.

Table generation processing as illustrated in FIG. 5 is implemented by the CPU 16A of the control device 16 of the ophthalmic device 110 executing a table generation processing process included in the data processing program 17A.

The table generation processing illustrated in FIG. 5 is performed by a generation section 200 of the CPU 16A.

First, at step S100, the generation section 200 confirms installation of a model eye in the ophthalmic device 110. In this case confirmation is made by a doctor or an operator operating the input/display device 16E to instruct finishing of installation of the model eye. Next, a scan range is set at step S102. The scan range is a range for scanning signal light when acquiring an OCT image in the ophthalmic device 110, namely a range of scan angles. Next, an initial value is set for the scan angle at step S104. The initial value is a given scan angle predetermined for when scanning in the scan range set at step S102. For example, a maximum scan angle is set therefor.

At step S106, the model eye is scanned at the set scan angle, and the polarization state of signal light obtained by scanning is acquired and stored at step S108. More specifically, the polarization state of the signal light is measured and stored. A polarization measurement device such as a polarization camera or the like is employed to measure the polarization state. The polarization measurement device is preferably installed to the sensor 20B of the OCT unit 20.

Note that the sensor 20B of the OCT unit 20 according to the present exemplary embodiment includes a polarization measurement function, and is capable of operating as a polarization measurement device. A polarizer having a different azimuth angle for each pixel on an incident side of light of a line sensor or a two-dimensional sensor is attached to a polarization camera, which is an example of the polarization measurement device, and by letting only light of a polarization state of each respective specific azimuth angle pass through, is able to measure the azimuth angle (direction of polarization) as the polarization state of incident light. Moreover, a polarimeter may be employed as another example of a polarization measurement device. Namely, light is passed through the polarizer, and the polarization state of light is measured by rotating the polarizer.

Moreover, a model eye conforming to a standard is prepared, and a table TBw is set for each ophthalmic device 110. This thereby enables effects of variations in polarization state arising due to fluctuations in shape during elliptical mirror manufacture to be eliminated. This thereby enables effects of fluctuation in the polarization state in the optical system for each examined eye, elliptical mirror, or the like to be eliminated whichever ophthalmic device 110 is employed, enabling stable OCT imaging to be performed.

At step S110, an adjustment amount of the polarization adjustment section 20F that corresponds to the polarization state stored at step S108 is derived. More specifically, the polarization adjustment section 20F adjusts the polarization state according to a drive amount of the drive section 20E. The relationship between drive amount of the drive section 20E and the azimuth angle of polarization is known in advance, and the drive amount of the polarization adjustment section 20F corresponding to the polarization state is derived as the adjustment amount. For example, taking a scan angle in a direction along an optical axis passing through a center of the pupil and a center of the eyeball as a reference, the drive amount from the polarization state of signal light at this reference is taken as the adjustment amount. At step S112, the scan angle, polarization state, and adjustment amount are associated with each other and stored.

At step S114, determination is made as to whether or not scanning of the scan angles to cover the scan range as been completed, with processing transitioning to step S118 when affirmative determination is made and processing transitioning to step S116 when negative determination is made. The scan angle is updated at step S116, and processing returns to step S106. At step S118, each of the scan angles, polarization states, and adjustment amounts associated with each other at step S112 are generated as the table TB and stored.

FIG. 6 illustrates a table TBw as an example of a table TB. In the table TBw of the example illustrated in FIG. 6, scan angles θ determining scan positions, polarization states PZ corresponding to the scan angles, and adjustment amounts W of the polarization adjustment section 20F are associated with each other. The table TBw is stored as the table TB in the storage device 17 of the control device 16. In the table TBw of the example illustrated in FIG. 6, a scan angle θ of a direction along an optical axis passing through the center of the pupil and the center of the eyeball is taken as a reference (0 degrees), and the polarization states PZ of signal light and adjustment amounts W, which are drive amounts to drive the polarization adjustment section 20F, are associated with each other for cases in which the scan angle θ is increased/decreased by 10 degree intervals.

Note that the example illustrated in FIG. 6 illustrates an example of a range of scan angles of ±70 degrees as the table TB, however the range of scan angles are not limited to those illustrated in FIG. 6. For example, a specific range may be set so as to be a range of scan angles of ±75 degrees and ±80 degrees, and may be set as a range of scan angles of ±100 degrees corresponding to the field of view of a examined eye. The range of scan angles is not limited to being set evenly about a reference (0 degrees) and may, for example, be set with different scan angle for the maximum value on the plus side and/or the minimum value on the minus side, moreover, for example, an angle range that is a part of a range of scan angles of ±100 degrees may be set.

Moreover, although in FIG. 6 an example of a table TB is illustrated in which scan angles θ for every 10 degrees, polarization states PZ of signal light, and adjustment amounts W are associated with each other, the table TB is not limited to correspondence relationship between scan angles θ for every 10 degrees, polarization states PZ of signal light, and adjustment amounts W. For example, intervals of less than 10 degrees may be employed, or more than 10 degrees may be employed.

Note that the generated table TB may be transmitted to the server 140, and may be acquired from the server 140. The table data may be derived and stored when setting up such as during device installation, or may be stored in the server 140 and acquired therefrom.

(2) OCT Imaging Using Table Polarization Information

Next, description follows regarding image processing by the ophthalmic device 110 using OCT.

Figure 7:
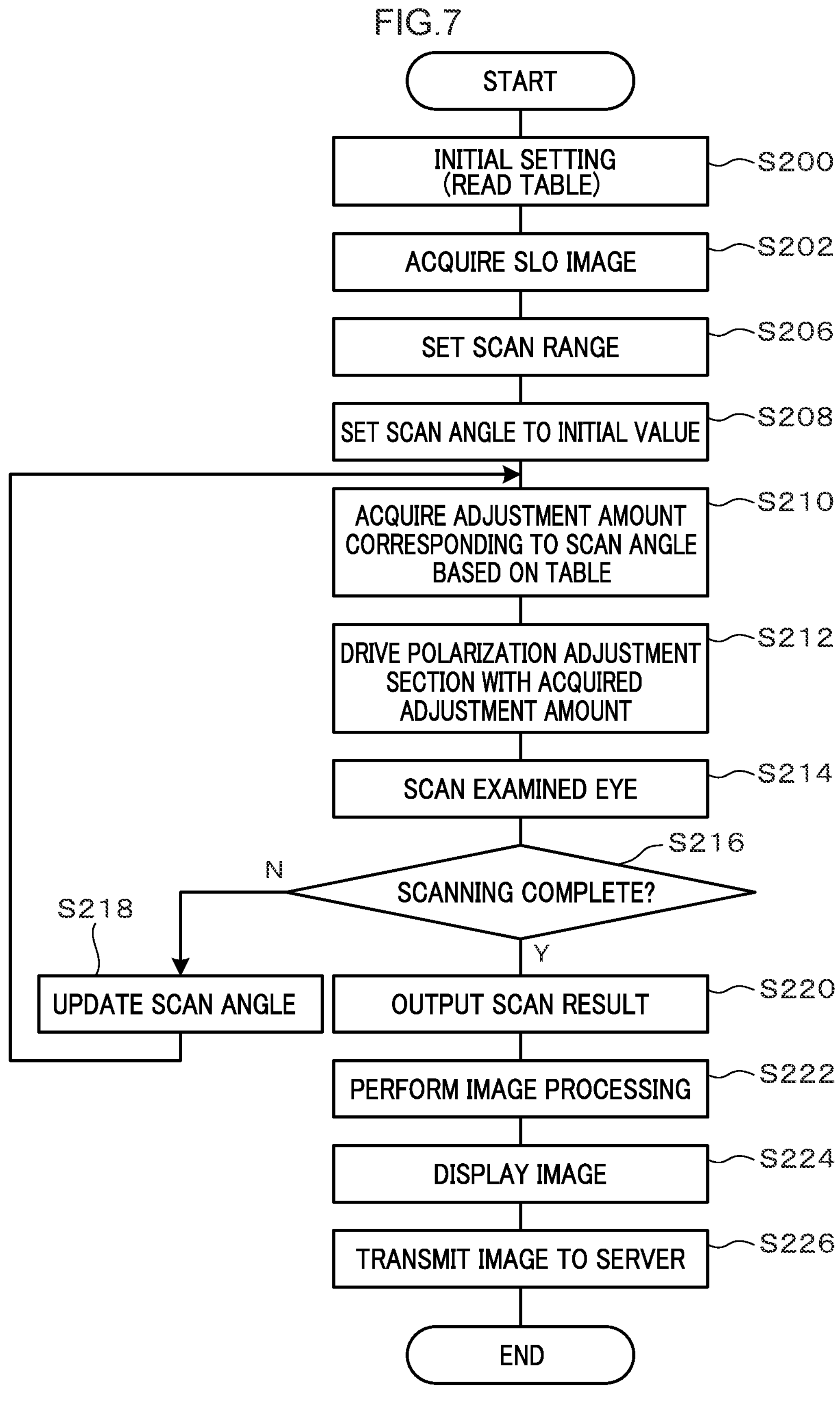
FIG. 7 is flowchart illustrating an example of a flow of image processing by OCT.

The OCT imaging processing illustrated in FIG. 7 is implemented by the CPU 16A of the control device 16 of the ophthalmic device 110 executing the OCT imaging processing process included in the data processing program 17A.

In the OCT imaging processing illustrated in FIG. 7, first at step S200, the setting section 202 performs initial setting. More specifically, as an initial setting, for example, processing is selected to adjust the optical system such as the focus, alignment, and the like in the ophthalmic device 110, to perform control so that eye tracking follows eye movements, and to receive input of identification information of the examinee. Moreover, at step S200 processing is performed to read the above table TB.

Next at step S202, the SLO image acquisition section 204 acquires an SLO image by executing imaging by SLO, and then processing transitions to step S208. The processing of step S202 is executed by the SLO image acquisition section 204, and a live SLO image is displayed on the input/display device 16E. The SLO image is displayed as a live view image on the input/display device 16E.

The OCT image acquisition section 206 acquires an OCT image by steps S206 to S224. More precisely, first at step S206, the image acquisition section 210 receives specification of a scan range that is an OCT imaging range. More specifically, the live SLO image displayed as the live view image on the input/display device 16E is viewed by an operator, and a location to perform OCT imaging is confirmed based on data representing an instruction. The operator sets the ophthalmic device 110 such that imaging by OCT is performed at the confirmed location. More specifically, for example, an operator operates a mouse, and instructs a scan range 872 that is the OCT imaging range. Namely, at step S206, the image acquisition section 210 receives specification of the scan range 872. A line of a B-scan is specified by the scan range 872. Note that the OCT imaging range may be specified as a rectangular range of a C-scan.

OCT imaging of the scan range 872 is performed in steps S208 to S220 with common polarization states for both the signal light and the reference light. More specifically, at step S208, the image acquisition section 210 sets the scan angle to an initial value. The initial value of the scan angle is, for example, set as the maximum value or minimum value of scan angle in the scan range. Next at step S210, a polarization adjustment amount corresponding to the scan angle is acquired with reference to the table TB, and at step S214 the examined eye is scanned in a state in which, for the set scan angle, the polarization state of the reference light has been adjusted so as to be common to the polarization state of the signal light Next at step S216, the image acquisition section 210 determines whether or not scanning of the scan range has finished. In cases in which negative determination is made at step S216, the scan angle is incremented or decremented at step S218, and processing is returned to step S210 and the above processing repeated. Processing transitions to step S220 in cases in which scanning of the scan range has finished and affirmative determination has been made at step S216. At step S220, the image acquisition section 210 outputs a detection signal of interference light obtained by scanning the scan range to the image processing section 212.

At step S222, the image processing section 212 performs signal processing such as Fourier transformation on the interference light detection signal, and generates OCT data configured from plural A-scan data. Then image processing such as arithmetic averaging processing, eyeball shape correction processing, and the like is performed on the OCT data, and a tomographic image is generated. After the tomographic image has been generated, processing transitions to step S224.

At step S224, the image display section 214 displays on the input/display device 16E the tomographic image obtained by subjecting to the image processing through executing the processing of step S222, and then the current processing transitions to step S226.

Figure 8:
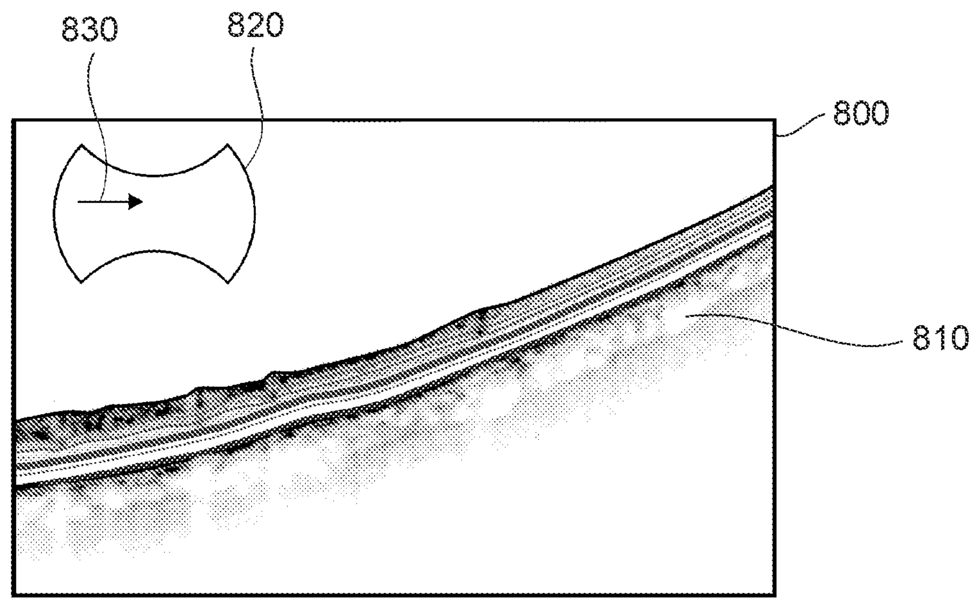
FIG. 8 is a diagram illustrating an example of a display screen including a tomographic image.

FIG. 8 illustrates a tomographic image displayed on the input/display device 16E. A display screen 800 includes a tomographic image 810, and a navigation image in which an arrow: 830 indicating position information of the tomographic image is displayed overlaid on a shrunk SLO image 820 as position information related to the position where the OCT data was acquired.

At step S226, the transmission section 208 transmits image data representing the tomographic image obtained by subjecting to the image processing through executing the processing of step S222 to the server 140 together with identification information of the examinee, and then ends the current data processing. Note that a configuration may be adopted so as to send OCT data to the server 140 together with this image data.

Content of control at above step S212 is an example of content of control by a control section of technology disclosed herein.

The server 140 transmits image data and the like to the viewer 150 based on requests from the viewer 150. Based on the image data, the viewer 150 displays an SLO image and an OCT image that are examined eye images on the display 156. A user is able to perform diagnostics on the examined eye 12 while looking at the SLO image and OCT image displayed on the display 156.

In the technology disclosed herein as described above, the signal light is scanned, the return light of signal light that has been reflected at the retina of the fundus of the examined eye is caused to interfere with the reference light branched from the signal light, and the polarization state of the reference light is adjusted according to the scan angle so as to cause interference when imaging a retinal depth direction tomographic region at each scan position. Thus the technology disclosed herein is able to maintain stable polarization states of the return light reflected at the retina and the reference light irrespective of scan angle when the tomographic region of the retina is being imaged while scanning the signal light. This thereby enables effects of different polarization due to scan angle to be eliminated from the interference light obtained from the return light reflected at the retina and the reference light. This means that when OCT imaging is being performed at a wide angle, effects of different polarization due to scan angle are eliminated, enabling a high resolution tomographic images to be acquired.

Second Exemplary Embodiment

Next description follows regarding a second exemplary embodiment. Note that the second exemplary embodiment is configured similarly to the first exemplary embodiment, and so the same reference numerals are appended to the same portions and detailed explanation thereof will be omitted.

In the first exemplary embodiment the polarization state of the polarization adjustment section 20F is measured, adjustment amounts of the polarization adjustment section 20F are derived from the measurement results and stored as a table. In the second exemplary embodiment, adjustment amounts of the polarization adjustment section 20F to optimize the polarization states are found by experimentation and stored as a table.

Figure 9:
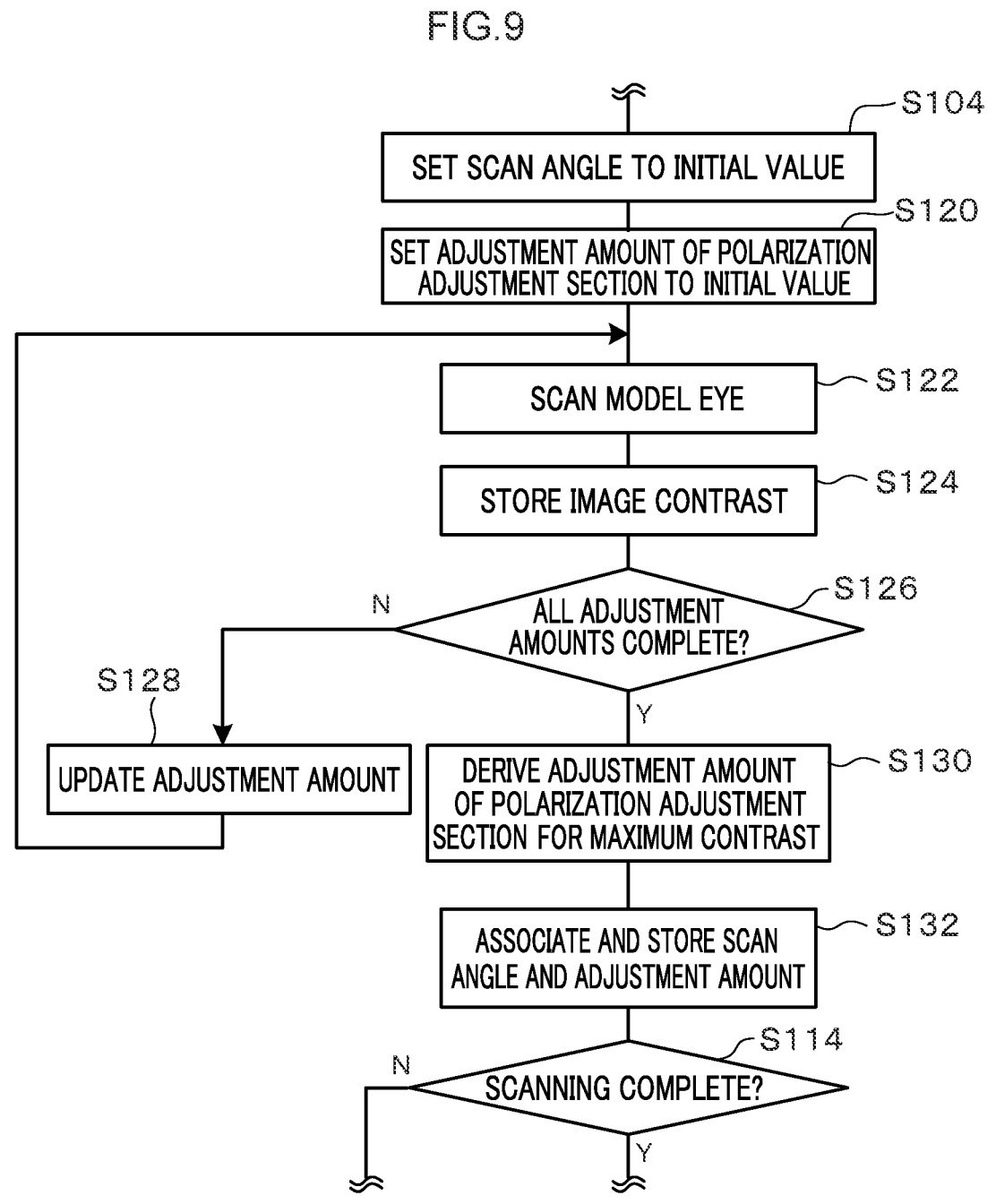

Next, description follows regarding processing to generate a table TB according to the present exemplary embodiment, with reference to FIG. 9.

The process of table generation processing illustrated in FIG. 9 substitutes processing from step S120 to step S132 for the processing from step S106 to step S112 in the table generation processing illustrated in FIG. 5. The table generation processing illustrated in FIG. 9 is performed by the generation section 200.

First, in the processing from step S100 to step S104, the generation section 200 sets a scan range, and sets an initial value of scan angle.

Figure 10:
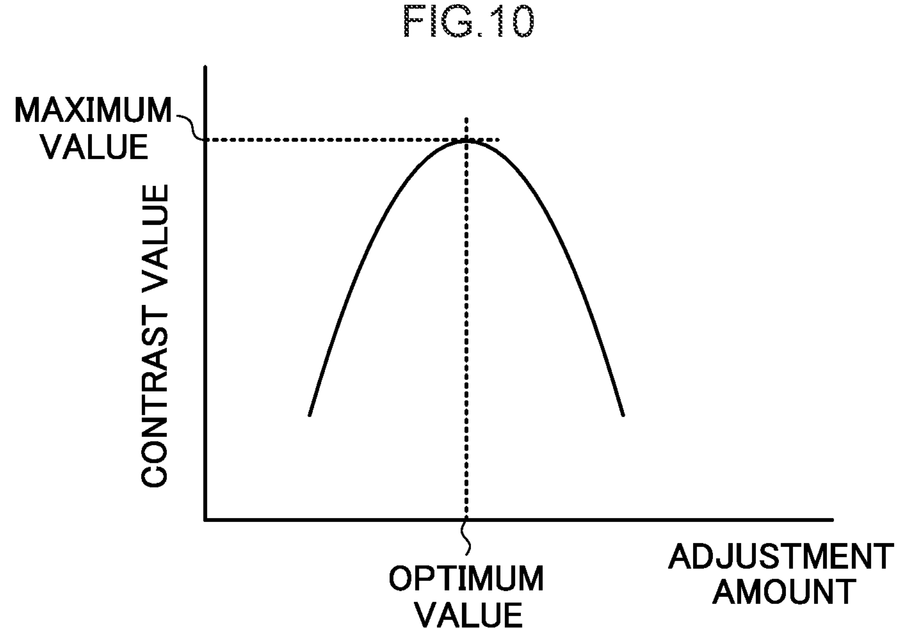
FIG. 10 is an explanatory diagram of an example related to deriving an optimum adjustment amount.

Then, at step S120, an adjustment amount of the polarization adjustment section 20F is set to an initial value. An example that may be given of the initial value is setting the azimuth angle of polarization to 0 degrees. Next at step S122, the model eye is scanned at the scan angle set at step S104, similarly to at step S106 of FIG. 5. At step S124, an image contrast from signal light obtained by scanning is acquired and stored as a polarization state of signal light. Next at step S126, determination is made as to whether or not the processing of step S122 to step S124 has been completed for the adjustable range of the polarization state of the polarization adjustment section 20F. In cases in which negative determination is made at step S126, the polarization adjustment section 20F is driven by a specific adjustment amount at step S128 so as to update the adjustment amount. More specifically, by setting a drive amount of the drive section 20E to a specific drive amount, the polarization state is adjusted to the updated adjustment amount. However, when affirmative determination is made at step S126, an optimum adjustment amount is derived at step S130. More specifically, as illustrated in FIG. 10, from out of plural image contrasts stored at step S124, an adjustment amount for maximum image contrast (indicated as an optimum value in FIG. 10) is derived as an adjustment amount of the polarization adjustment section 20F for the set scan angle. Then at step S132, the adjustment amount of the image contrast derived at step S130 and the scan angle are associated with each other and stored.

Then from step S114 to step S118, correspondence relationships between scan angles so as to cover the scan range and adjustment amounts are generated as the table TB and stored.

A table TBv is illustrated in FIG. 11 as an example of the table TB. In the table TBv of the example illustrated in FIG. 11, scan angles θ determining the scan position and adjustment amounts V of the polarization adjustment section 20F corresponding to these scan angles are associated with each other. The table TBv is stored as a table TB in the storage device 17 of the control device 16. In the table TBv of the example illustrated in FIG. 11, the scan angle θ in the direction along the optical axis passing through the center of the pupil and the center of the eyeball is taken as a reference (0) degrees), and adjustment amounts V, which are drive amounts to drive the polarization adjustment section 20F, are associated with each other for cases in which the scan angle θ is increased/decreased by 10 degree intervals.

Note that in the example illustrated in FIG. 11, similarly to in the example illustrated in FIG. 6, there is no limitation to using the range of scan angles of ±70 degrees as the table TB.

In the technology disclosed herein as described above, the adjustment amount to give the maximum contrast is derived based on the image contrasts obtained by driving the polarization adjustment section 20F and so the polarization state is adjusted according to actual devices.

First Modified Example

A case has been described above of an example of the OCT unit 20 in which the reference light optical system 20G includes the polarization adjustment section 20F of a ½ wavelength plate or the like. However, the technology disclosed herein is not limited thereto. In a first modified example, the reference light optical system 20G includes a depolarizer that emits incident light in a fixed polarization state as unpolarized light instead of the polarization adjustment section 20F of a ½ wavelength plate or the like.

Figure 12:
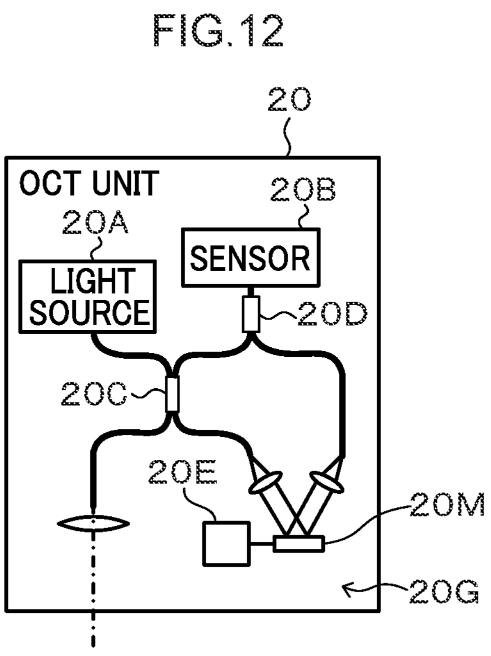
FIG. 12 is a block diagram illustrating an example of an OCT unit.

Next, description follows regarding the first modified example, with reference to FIG. 12.

As illustrated in FIG. 12, the modified example includes, as an example an OCT unit 20, and a reference light optical system 20G provided with a mirror type depolarizer 20M, instead of the polarization adjustment section 20F of the ½ wavelength plate or the like illustrated in FIG. 2

The other signal light branched by the fiber coupler 20C is adjusted in polarization state by being reflected at the mirror type depolarizer 20M, and is incident to the sensor 20B through the fiber coupler 20D. The depolarizer 20M is, as described above, coupled to the drive section 20E, and adjusts the polarization state of incident light according to the drive amount of the drive section 20E before emission.

Second Modified Example

As described above, an example of the OCT unit 20 has been described for a case in which the polarization adjustment section 20F of a ½ wavelength plate or the like is provided to the reference light optical system 20G on an optical path of the other light divided by the fiber coupler 20C. The technology disclosed herein is not limited to providing the polarization adjustment section 20F only to the reference light optical system 20G. For example, a polarization adjustment section 20F may be provided between the fiber coupler 20C and the fiber coupler 20D that are on the optical path of return light of the signal light, more specifically on the optical path of return light toward the sensor 20B. Moreover, the polarization adjustment section 20F may be provided on both the optical path of the other light divided by the fiber coupler 20C, and the optical path of return light toward the sensor 20B.

Third Modified Example

An example has been described in which an SLO image (UWF SLO image) is used to determine an OCT imaging position, however it goes without saying that a fundus image by a fundus camera may be employed, and fundus images imaged by various ophthalmic devices, such as an SLO ophthalmic device or a fundus camera having a comparatively small angle of view (for example an internal illumination angle of 100 degrees or less), may be applied therefor.

Fourth Modified Example

A case has been described above in which the polarization state is adjusted for at least one of the polarization state of signal light or the polarization state of reference light so as to achieve a common polarization state for both the signal light according to the scan angle and the reference light. However, the technology disclosed herein is not limited to adjusting the polarization state according to the scan angle and, for example, the polarization state may be adjusted according to the scan position on the fundus of the examined eye so as to achieve a common polarization state for both the signal light and the reference light. For example, the polarization state may be adjusted, in A-scan units, for at least one out of the polarization state of the signal light and the polarization state of the reference light so as to achieve a common polarization state for both the signal light and the reference light.

Other Modified Examples

In the above exemplary embodiments examples has been described of the ophthalmic system 100 provided with the ophthalmic device 110, the eye axial length measurement device 120, the server 140, and the viewer 150, however the technology disclosed herein is not limited thereto. For example, as a first example, the eye axial length measurement device 120 may be omitted.

Moreover, as a second example, the ophthalmic device 110 may further include the function of at least one of the server 140 or the viewer 150. This thereby enables at least one device out of the server 140 or the viewer 150 corresponding to the function provided to the ophthalmic device 110 to be omitted.

Furthermore, the server 140 may be omitted, and the viewer 150 configured so as to execute the functions of the server 140.

Note that although the ophthalmic device 110 according to the technology disclosed herein has be described for an OCT unit in which swept source OCT (SS-OCT) is employed, application may be made to an ophthalmic device employing another type other than swept-source, such as spectral domain OCT (SD-OCT) for example.

Moreover, although the technology disclosed herein has been described for the ophthalmic device 110 including an SLO imaging system function and an OCT imaging system function, an OCT unit including a configuration according to the technology disclosed herein may be combined with a fundus imaging device such as a fundus camera or the like, a slit lamp, an ophthalmic surgery microscope, or the like.

Moreover, the technology disclosed herein may be applied to a standalone OCT device configured from a control device, an OCT unit, and a wide angled optical system. A standalone OCT device is an ophthalmic instrument specialized for acquiring OCT images of examined eyes. In a standalone OCT device, an en face image generated from OCT volume data may be employed instead of an SLO image when deciding the OCT imaging position.

The data processing described in the above exemplary embodiments are merely examples thereof. Thus it goes without saying that unnecessary steps may be omitted, new steps may be added, and the sequence of processing may be changed within a scope not departing from the spirit of technology disclosed herein.

Moreover, although in the exemplary embodiment described above employing a CPU was described as an example of an ordinary processor, in the above "processor" indicates a wide definition of processors and includes general processors (for example, a central processing unit (CPU) or the like), and specialized processors (such as a graphics processing unit (GPU), an application specific integrated circuit (ASIC), a field programmable gate array (FPGA), a programmable logic device, or the like).

Moreover, processor operations in the above exemplary embodiments may be performed by a single processor, may be performed by linking plural processors together, or may be performed by plural processors present at physically distinct positions cooperating with each other.

Although in the above exemplary embodiment a case is presented as an example in which data processing is implemented using a software configuration using a computer, the technology disclosed herein is not limited thereto. For example, instead of a software configuration employing a computer, the data processing may be executed using a hardware configuration alone, such as with FPGAs, ASICs, etc. Alternatively some processing in the data processing may be executed by a software configuration, and the remaining processing therein may be executed by a hardware configuration.

Furthermore, in order to execute the processing of the above exemplary embodiments with a computer, the above processing may be distributed by storing a program written with computer executable code on a storage medium such as an optical disk or the like.

All cited documents, patent applications, and technical standards mentioned in the present specification are incorporated by reference in the present specification to the same extent as if each individual cited document, patent application, or technical standard was specifically and individually indicated to be incorporated by reference.

The invention claimed is:

1. An ophthalmic device comprising:

an interference optical system that detects interference light between signal light obtained by scanning an examined eye with light from a light source and reference light configured from light divided from the light source;

an adjustment section that is disposed on an optical path of at least one of the signal light or the reference light, and that adjusts a polarization state of light propagating along the at least one optical path such that a polarization state of the signal light is the same as a polarization state of the reference light; and a control section that controls the adjustment section according to a scan angle at which the examined eye is scanned.

2. The ophthalmic device of claim 1, wherein the control section performs control to adjust the polarization state of the at least one optical path according to a position scanned on the examined eye corresponding to the scan angle at which the examined eye is scanned.

3. The ophthalmic device of claim 1, wherein the adjustment section includes an optical member to adjust a direction of polarization.

4. The ophthalmic device of claim 3, wherein the optical member includes a ½ wavelength plate and adjusts the direction of polarization, by rotating the ½ wavelength plate.

5. The ophthalmic device of claim 3, wherein the optical member includes a reflection member to adjust an optical path length, and adjusts the direction of polarization by adjusting a position of the reflection member in an optical axis direction.

6. The ophthalmic device of claim 3, wherein the optical member includes a depolarizer, and adjusts the direction of polarization by using the depolarizer to emit unpolarized light.

7. The ophthalmic device of claim 1, wherein the control section:

detects the scan angle at which the examined eye is scanned; and computes an adjustment amount based on the detected scan angle.

8. The ophthalmic device of claim 7, wherein the adjustment section derives the adjustment amount based on a table pre-stored with scan angles at which the examined eye is scanned associated with adjustment amounts to adjust the polarization state.

9. A control method for controlling the ophthalmic device of claim 1, the control method comprising, by a processor of the ophthalmic device:

a step of acquiring an adjustment amount of the adjustment section that is disposed on the optical path of the at least one of the signal light or the reference light, and that adjusts the polarization state of the light propagating along the at least one optical path such that the polarization state of the signal light is the same as the polarization state of the reference light, wherein the adjustment amount corresponds to a scan angle of OCT signal light; and a step of controlling the adjustment section based on the adjustment amount.

10. A non-transitory storage medium storing a program that is executable by a computer to execute:

acquiring an adjustment amount of an adjustment section that is disposed on an optical path of at least one of a signal light or a reference light, and that adjusts a polarization state of light propagating along the at least one optical path such that a polarization state of the signal light is the same as a polarization state of the reference light, wherein the adjustment amount corresponds to a scan angle of OCT signal light; and controlling the adjustment section based on the adjustment amount.

* * * * *